(12) United States Patent
Wang

(10) Patent No.: US 11,938,241 B2
(45) Date of Patent: Mar. 26, 2024

(54) FOLDABLE PLANT LIGHT

(71) Applicant: Tiejun Wang, Lin'an (CN)

(72) Inventor: Tiejun Wang, Lin'an (CN)

( * ) Notice: Subject to any disclaimer, the term of this patent is extended or adjusted under 35 U.S.C. 154(b) by 2 days.

(21) Appl. No.: 17/879,323

(22) Filed: Aug. 2, 2022

(65) Prior Publication Data

US 2024/0042074 A1 Feb. 8, 2024

(51) Int. Cl.
A61L 2/10 (2006.01)
F21V 15/01 (2006.01)
F21Y 115/10 (2016.01)

(52) U.S. Cl.
CPC .............. *A61L 2/10* (2013.01); *F21V 15/01* (2013.01); *F21Y 2115/10* (2016.08)

(58) Field of Classification Search
CPC ......... A61L 2/10; F21V 15/01; F21Y 2115/10
See application file for complete search history.

(56) References Cited

U.S. PATENT DOCUMENTS

2011/0011045 A1* 1/2011 Ton ..................... F21V 33/0088
  55/385.1
2022/0047739 A1* 2/2022 Wade ....................... A61L 2/10

* cited by examiner

*Primary Examiner* — Jia X Pan
*Assistant Examiner* — Jessica M Apenteng
(74) *Attorney, Agent, or Firm* — Daniel M. Cohn; Howard M. Cohn

(57) ABSTRACT

An Air Quality Control Lighting Device incorporating a purification device in combination with a lighting device having a LED light panel, a cover installed above the light panel, the interior of the cover forms a cavity that encloses an air UV purification device, and the air UV purification device consisting of a plurality of UV lamps mounted atop the LED light panel.

17 Claims, 4 Drawing Sheets

FOLDABLE PLANT LIGHT

TECHNICAL FIELD

The present invention belongs to the technical field of lamps and especially relates to an LED lighting and UV lamp air purifier.

BACKGROUND OF THE INVENTION

The present invention relates to an efficient room lighting fixture with safe and effective air sterilization, and finds particular application in public spaces such as hospitals, health care institutions, dormitories, schools and offices. Short wave ultraviolet (UV-C) energy has long been used for air sterilization. The usefulness of UV-C irradiation on air quality lies in the effect on germs (microorganisms) transmitted in aerosolized form. Such infectious germs are generally less than 0.3 microns in diameter and are suspended or "float" in the air.

Different types of microorganisms vary significantly in their resistance to UV-C irradiation. For example, spores such as anthrax have a "cell wall" (like bacteria) as well as an outer "shell" which must be penetrated by the UV-C energy. Viruses such as influenza, the common cold, SARS, measles and smallpox do not have a cell wall and are about five times more susceptible to UV-C radiation than spores. Bacteria with a cell wall such as tuberculosis, even extended drug resistant (XDR) TB, may be ten times more vulnerable to UV-C radiation than anthrax spores. The UV-C "dose" needed to destroy germs is generally expressed as joules (one UV-C watt of energy for one second) per square meter; or the equivalent LLJ/cm micro-joules per square centimeter.

Because of safety considerations, air Sterilization products (e.g., in-duct, ceiling and floor mounted fixtures) generally avoid UV-C radiation into a room and have attempted to confine UV-C radiation to the interior of a closed (i.e., UV-C baffled) chamber, and pass air through the baffled chamber for sterilization.

A significant factor in avoiding excessive UV-C radiation in the lower part of a room, i.e. the part of the room populated by people, is the height at which the UV-C device is located.

For example, unbaffled floor and table mounted devices would emit direct UV-C radiation into the lower part of the room. Energy cost considerations have reduced ceiling heights, typically to eight feet, which exacerbates the dilemma of achieving an effective UV-C dose in the upper part of the room without exceeding acceptable limits in the lower part of the room.

Initial efforts to use wall and ceiling pendant UV-C fixtures transmitted an intense UV-C beam at a room height well above the "eye level of people occupying the room, i.e., generally considered to be approximately 60 inches above the floor. Germ reduction occurred in the air. passing through the beam as a result of convection currents and ventilation systems. While the intensity of the beam was effective in sterilizing the air passing through the beam, the volume and velocity of the air passing through the beam was not controlled and, being thus subject to external forces, such devices have generally been ineffective. In addition, the narrowing of the beam vertically, typically through the use of louvers, wasted most of the UV-C energy making such fixtures highly inefficient.

SUMMARY OF THE INVENTION

An Air Quality Control Lighting Device incorporating a purification device in combination with a lighting device having a LED light panel, a cover installed above the light panel, the interior of the cover forms a cavity that encloses an air UV purification device, and the air UV purification device consisting of a plurality of UV lamps mounted atop the LED light panel.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1:
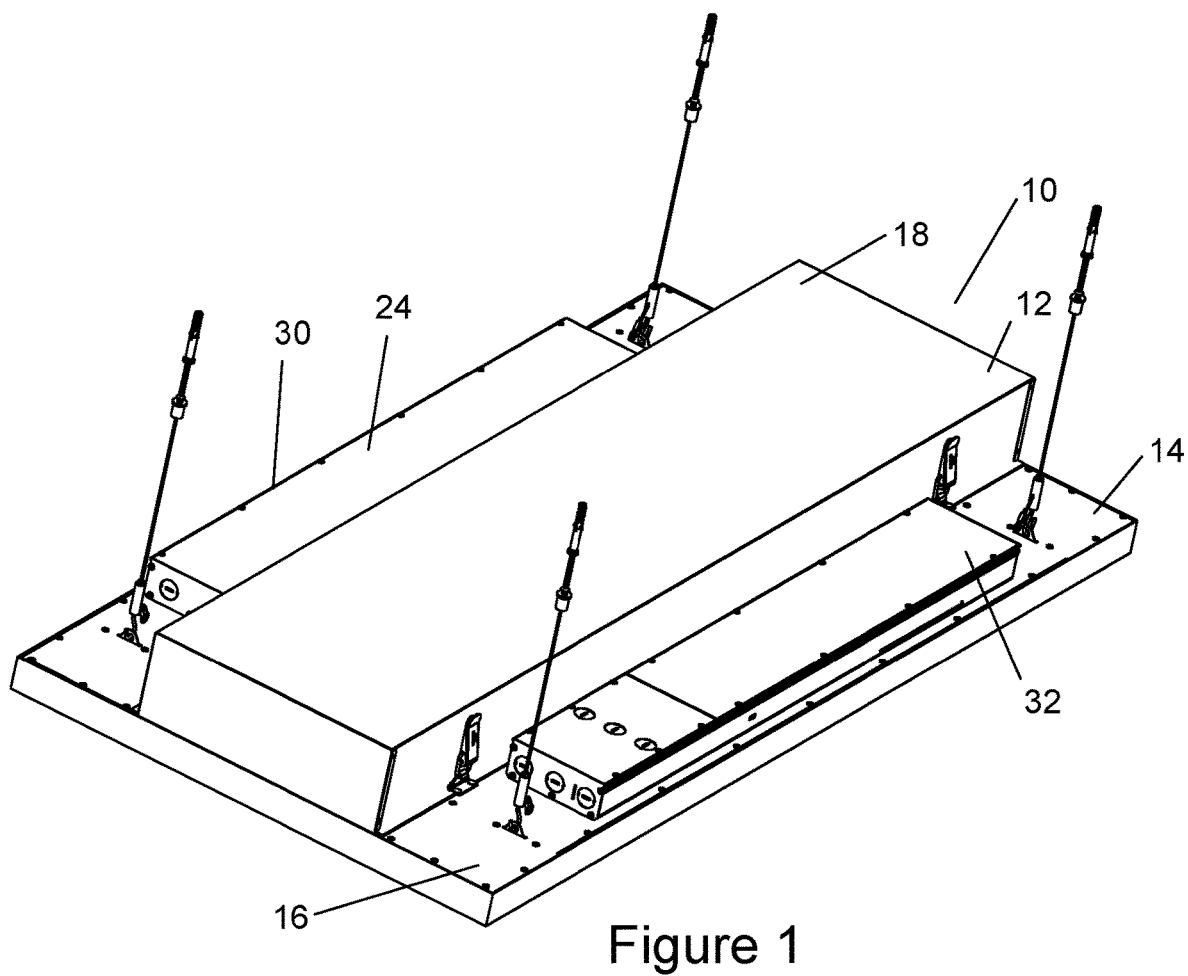

In some cases, similar elements may be referred to by similar numbers in various figures (FIGs) of the drawing, in which case typically the last two significant digits may be the same, the most significant digit being the number of the drawing figure (FIG). Furthermore, for clarity, some reference numbers may be omitted in certain drawings.

Figure 2:
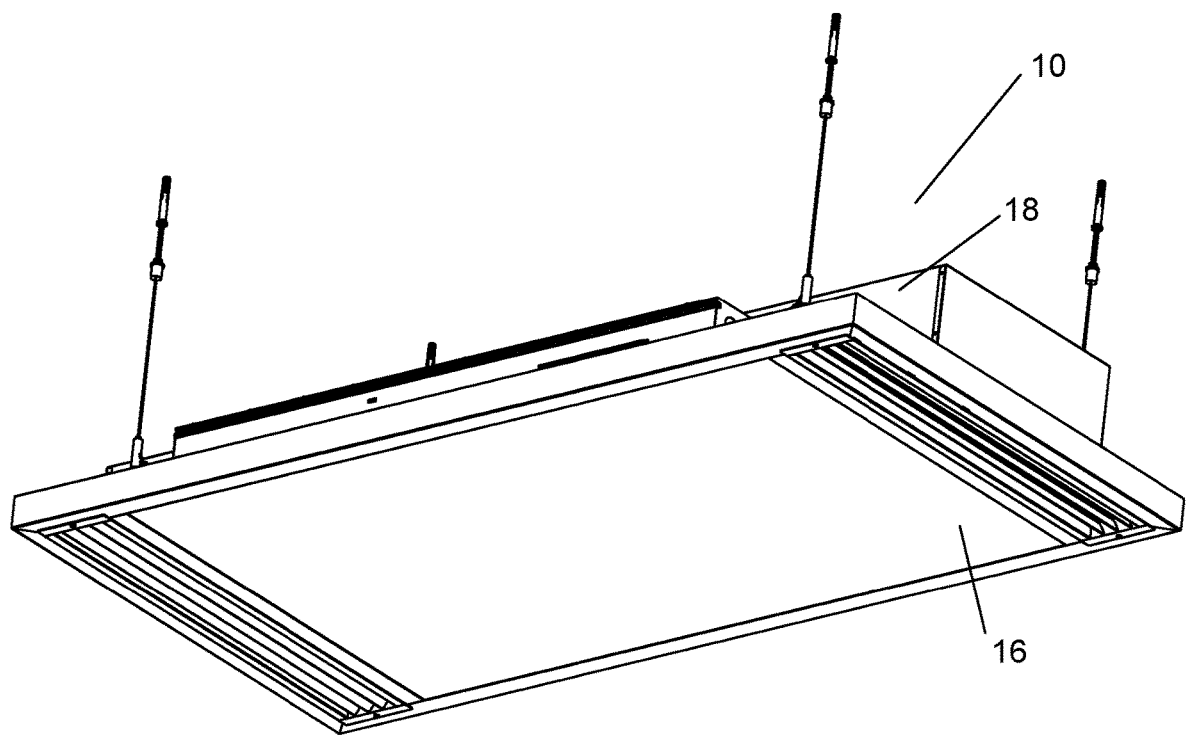
Figure 3:
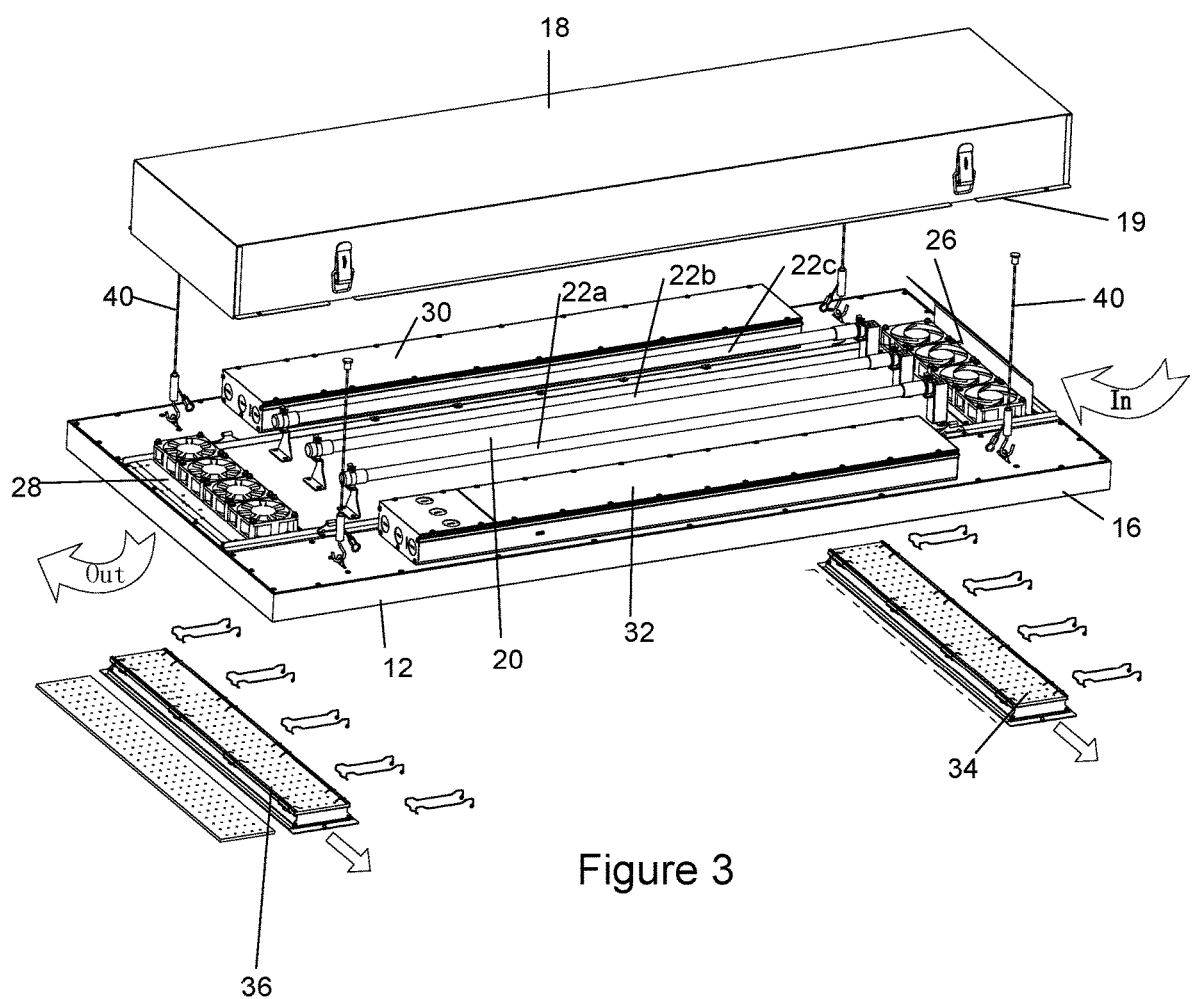
Figure 4:
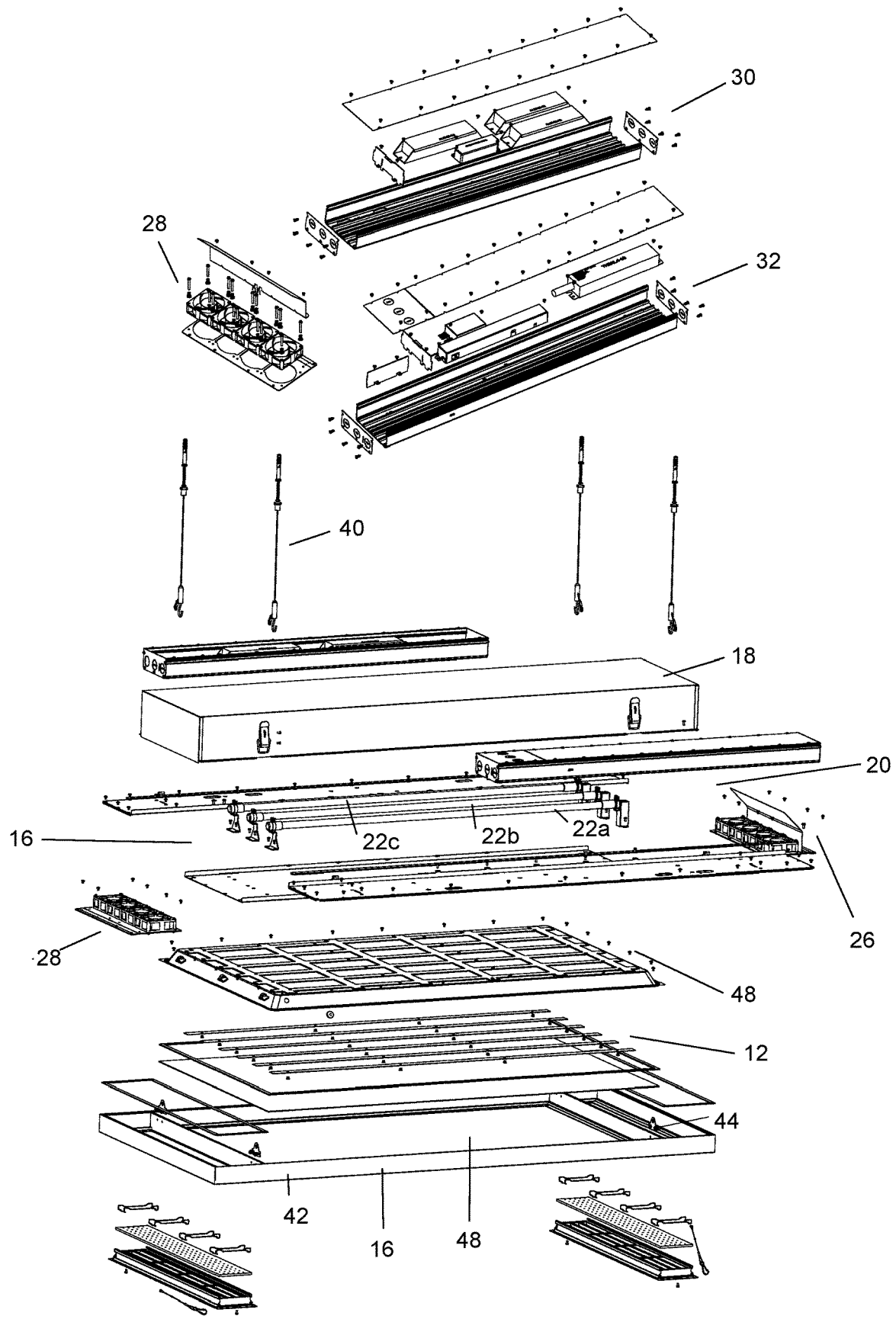

FIG. 1 is a three-dimensional top view of a purification device in combination with a lighting device, according to the present invention;

FIG. 2 is a bottom view of a UV purification device in combination with an LED lighting device, according to the present invention;

FIG. 3 is a three-dimensional, exploded side top view of a purification device in combination with a lighting device, according to the present invention; and FIG. 4 is a three-dimensional, exploded side top view of a purification device in combination with a lighting device, according to the present invention;

DETAILED DESCRIPTION

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader and should not in any way be interpreted as limiting.

Referring to FIG. 1, there is shown a three-dimensional view of an Air Quality Control Lighting Device 10 incorporating a purification device 12 in combination with a lighting device 14. Air Quality Control Lighting Device 10 includes a LED light panel 16. A cover 18 is installed above the light panel 16 and forms a cavity 19 that encloses an air UV purification device 20 consisting of a plurality of UV lamps 22, such as three UV lamps 22a, 22b and 22c (22a-22c) mounted atop the LED light panel 12. A low-voltage power supply 24 drives an air inlet fan 26 and the air outlet fan 28, interconnects with various sensing devices, automatically detects the air quality, and automatically controls the fans to work to maintain high quality air. The fans 26 and 28 allow the air to flow through the UV purification device 20 in a stable flow to achieve sterilization and purification of the air. The UV lamps 22a-22c provide a synchronous relationship and power interface for a built-in audio.

A UV lamp ballast 30 drives at least one UV lamp tube 22a-22c The UV lamp tubes 22a-22c can work in any combination, work synchronously with the inlet and outlet fans 26 and 28. The UV ballast 30 can work alone or at the same time with the LED lighting (light panel 16). The ballast 30 integrates a low voltage, constant voltage source and an abnormal status indication function.

The LED driver 32 is disposed behind the grouper. A group of outputs of the grouper control the LED lighting and provide CCT and lumen adjustment. Further, the group of outputs can meet the requirement of work, life lighting and scene lighting. In addition, the group of outputs can operate at low voltage and provide a constant voltage interface which can be connected to various sensors. The group of outputs can operate and automatically adjust the color temperature and lumens. It can also cooperate with the data collector to realize energy savings and intelligent lighting.

Referring to FIG. 3, the UV device 20 is a carrier that disinfects airflow. The air flows into and runs through the air inlet fan 26. The air is directed thorough a cotton filter 34 and then flows through the UV disinfection cavity below the UV lamp cover 18. When the UV lamp(s) are on, the air is disinfected as it flows through the disinfection cavity and then is blown out by the air outlet fan 28 and if desired, passed through a replaceable cotton filter 36. The filters 34 and 36 can be a cotton filter through which the air passes as it is moved through the air inlet and outlet fans 26 and 28. After a period of time, the cotton air filters 34 and 36 can become clogged but are easily replaced.

A grouper and a receiver, at least two outputs, control LED lighting and UV lamp work can be controlled by Wi-Fi or remote control. Blue tooth, a sensor, a voice activated smart device, a wire or wireless switch device can control automatic start or delay off. LED lighting and UV lamp can work at the same time or separately.

Referring to FIG. 3, the Air Quality Control Lighting Device 10 can be suspended by 4 wires 40 which are removably mounted to the connected to the LED light panel 16.

Referring to FIG. 4, The light panel 16 includes a frame 42 having rectangular openings 44 and 46 at either end which receive the air inlet and outlet fans 26 and 28, respectively. A rectangular opening 48 between the rectangular openings 44 and 46 receives the LED light panel 12 and is held in place by a screen 48.

In operation, the air purification process is initiated by starting the power to the purification and lighting device 10 either manually or remotely. After starting the air inlet and outlet fans 26 and 28, the UV tubes 22a-22c. Air is drawn in through the cotton filter 34 in the air inlet fan 26. The filtered air enters the lighted UV lamp 16 and is purified in the cavity formed below the cover 38 which houses the lamps 16. The air enters a long channel below the cover 38 which is lit by the UV lamps. The air flows through inlet openings 40 which direct the air through the air filter disposed below the inlet fan 26. The air enters flow through the space or channel below the cover 38, across the UV lamps 16 and through the air filter 36, disposed in the outlet fan 28 and through the outlet openings 42.

The purification provides a UV lamp that can not only purify air but provide a light for lighting a space. The device has a remote-control function which can cause the lighting device and the air purification device to work separately or at the same time.

It is to be understood that the above-described embodiments of the present invention are merely illustrative of or explaining the principles of the invention and are not to be construed as limiting the invention. Therefore, any modification, equivalent replacement, improvement and the like made without departing from the spirit and scope of the present invention should be included in the protection scope of the present invention. Further, it is intended that the appended claims cover all such variations and modifications as fall within the scope and boundaries of the appended claims or the equivalents of such scope and boundaries,

The invention claimed is:

1. An Air Quality Control Lighting Device incorporating a purification device in combination with a lighting device, comprising:
   a LED light panel;
   a UV lamp cover installed above the LED light panel;
   the interior of the UV lamp cover forms a cavity that encloses an air UV purification device: and
   the air UV purification device consisting of a plurality of UV lamps mounted atop the LED light panel;
   a power supply that drives an air inlet fan located at one end of the LED light panel and an air outlet fan located at an opposite end the LED light panel;
   the air inlet fan and the air outlet fan cause air to flow through the UV purification device in a stable flow to achieve sterilization and purification of the air;
   wherein air is directed thorough a first cotton filter in the air inlet fan and into the UV disinfection cavity below the UV lamp cover whereby the air is disinfected in the UV disinfection cavity below the UV lamp cover; and
   the air disinifected in the UV disinfection cavity directed thorough an air outlet fan having a second cotton filter and away from the disinfection cavity.

2. The Air Quality Control Lighting device of claim 1 including the power supply that drives the air inlet fan and the air outlet fan that cause air to flow through the UV purification device in a stable flow to achieve sterilization and purification of the air.

3. The Air Quality Control Lighting device of claim 2 wherein the power supply interconnects with a plurality of sensing devices.

4. The Air Quality Control Lighting device of claim 3 wherein the power supply is a low voltage power supply.

5. The Air Quality Control Lighting device of claim 3 wherein the sensing devices automatically detect the air quality.

6. The Air Quality Control Lighting device of claim 5 wherein the sensing devices automatically controls the air inlet fan and an air outlet fan to maintain high quality air in response to the detected air quality.

7. The Air Quality Control Lighting device of claim 6 wherein the UV lamps provide a synchronous relationship and power interface for a built-in audio output.

8. The Air Quality Control Lighting device of claim 7 wherein the plurality of UV lamps includes three lamps.

9. The Air Quality Control Lighting device of claim 8 wherein a UV lamp ballast drives at least one of the plurality of UV lamp tubes.

10. The Air Quality Control Lighting device of claim 9 wherein the UV lamp ballast drives each of the plurality of UV lamp tubes.

11. The Air Quality Control Lighting device of claim 10 wherein the UV lamp tubes can work in any combination.

12. The Air Quality Control Lighting device of claim 11 wherein the UV lamp tubes work synchronously with the inlet and outlet fans.

13. The Air Quality Control Lighting device of claim 12 wherein the UV ballast can work alone.

14. The Air Quality Control Lighting device of claim 13 wherein the UV ballast can work at the same time with the LED lighting.

15. The Air Quality Control Lighting device of claim 14 wherein the UV ballast integrates a low voltage, constant voltage source and an abnormal status indication function.

16. The Air Quality Control Lighting device of claim 15 including a LED driver disposed behind a grouper having a group of outputs that control the LED lighting and provide CCT and lumen adjustment.

17. The Air Quality Control Lighting device of claim 16 wherein the group of outputs can operate and automatically adjust the color temperature and lumens.

* * * * *